United States Patent
Scherich et al.

(10) Patent No.: US 12,285,575 B2
(45) Date of Patent: *Apr. 29, 2025

(54) CATHETER STABILIZATION PLATFORM, SYSTEMS, AND METHODS

(71) Applicant: Becton, Dickinson and Company, Franklin Lakes, NJ (US)

(72) Inventors: Megan Scherich, Salt Lake City, UT (US); Curtis H. Blanchard, Riverton, UT (US); Nathan Mitchell, Murray, UT (US); Tyler Warner, Bluffdale, UT (US); David Myers, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/208,730

(22) Filed: Jun. 12, 2023

(65) Prior Publication Data

US 2023/0321405 A1    Oct. 12, 2023

Related U.S. Application Data

(63) Continuation of application No. 16/547,926, filed on Aug. 22, 2019, now Pat. No. 11,717,650.

(Continued)

(51) Int. Cl.
*A61M 25/06*    (2006.01)
*A61M 25/00*    (2006.01)
(Continued)

(52) U.S. Cl.
CPC .... *A61M 25/0631* (2013.01); *A61M 25/0606* (2013.01); *A61M 25/0637* (2013.01);
(Continued)

(58) Field of Classification Search
CPC .......... A61M 25/0637; A61M 25/0097; A61M 25/02; A61M 2025/028; A61M 2005/1586; A61M 2025/024
See application file for complete search history.

(56) References Cited

U.S. PATENT DOCUMENTS 1,588,918 A    6/1926    Taylor
8,162,898 B1 *  4/2012    Wright .................. A61M 5/158
                                                    604/179
(Continued)

FOREIGN PATENT DOCUMENTS

CN    1119417 A    3/1996
CN    1175906 A    3/1998
(Continued)

*Primary Examiner* — William R Carpenter
*Assistant Examiner* — Robert F Allen
(74) *Attorney, Agent, or Firm* — Kirton McConkie; Whitney Blair; Kevin Stinger

(57) ABSTRACT

An attachment for a catheter assembly may include a platform, which may include an upper surface and a bottom surface. The bottom surface may be configured to contact skin of a patient. At least a portion of the upper surface may be configured to support the catheter assembly. The upper surface may support the catheter assembly at an angle with respect to skin of the patient that is approximately equal to an insertion angle of a catheter of the catheter assembly. The attachment may include snap feature coupled to the upper surface of the platform. The attachment may include a blunt cannula extending distally from the snap feature. The blunt cannula and the portion of the upper surface may provide a generally straight pathway for an instrument inserted distally through the attachment into the catheter assembly.

20 Claims, 5 Drawing Sheets

Related U.S. Application Data

(60) Provisional application No. 62/729,297, filed on Sep. 10, 2018.

(51) Int. Cl.
*A61M 25/02* (2006.01)
*A61M 39/06* (2006.01)
*A61M 39/10* (2006.01)

(52) U.S. Cl.
CPC ......... *A61M 25/0097* (2013.01); *A61M 25/02* (2013.01); *A61M 2025/024* (2013.01); *A61M 25/0625* (2013.01); *A61M 25/0662* (2013.01); *A61M 25/0693* (2013.01); *A61M 2039/062* (2013.01); *A61M 2039/0626* (2013.01); *A61M 39/10* (2013.01); *A61M 2039/1072* (2013.01)

(56) References Cited

U.S. PATENT DOCUMENTS

| | | |
|---|---|---|
| 9,402,977 B2 | 8/2016 | Wenderow et al. |
| 9,717,885 B1 | 8/2017 | Narciso Martinez |
| 11,097,083 B2 | 8/2021 | Burkholz et al. |
| 2006/0015131 A1 | 1/2006 | Kierce |
| 2007/0265571 A1* | 11/2007 | Utterberg ............... A61M 25/02 604/174 |
| 2009/0125003 A1 | 5/2009 | Hawkins |
| 2009/0149814 A1* | 6/2009 | Bailey ................... A61M 25/02 604/180 |
| 2010/0234804 A1* | 9/2010 | Hiejima ............ A61M 25/0625 604/110 |
| 2010/0298777 A1* | 11/2010 | Nishtala ................ A61M 39/10 604/174 |
| 2012/0016312 A1* | 1/2012 | Brown .................. A61M 25/02 604/174 |
| 2012/0016345 A1 | 1/2012 | Carter |
| 2012/0215173 A1 | 8/2012 | Wright |
| 2013/0138080 A1 | 5/2013 | Andino et al. |
| 2014/0135703 A1* | 5/2014 | Yeh ................... A61M 25/0693 604/533 |
| 2014/0364810 A1 | 12/2014 | Knobloch |
| 2017/0120012 A1 | 5/2017 | Sonderegger |
| 2017/0239443 A1 | 8/2017 | Abitabilo et al. |
| 2017/0296782 A1 | 10/2017 | Bornhoft et al. |
| 2018/0318557 A1 | 11/2018 | Burkholz et al. |
| 2018/0339132 A1* | 11/2018 | Brunetti .................. A61M 5/14 |
| 2019/0177942 A1 | 6/2019 | Serna garcia-conde et al. |
| 2019/0275312 A1 | 9/2019 | Chelak |
| 2020/0154112 A1 | 5/2020 | Kopietz |
| 2022/0001161 A1 | 1/2022 | Burkholz et al. |
| 2023/0099120 A1 | 3/2023 | Hu et al. |

FOREIGN PATENT DOCUMENTS

| | | | |
|---|---|---|---|
| CN | 1282259 A | 1/2001 | |
| WO | WO-9421319 A1 * | 9/1994 | ............ A61M 25/02 |
| WO | 0191847 A2 | 12/2001 | |

* cited by examiner

CATHETER STABILIZATION PLATFORM, SYSTEMS, AND METHODS

RELATED APPLICATIONS

This application is a continuation of U.S. patent application Ser. No. 16/547,926, filed Aug. 22, 2019, and entitled CATHETER STABILIZATION PLATFORM, SYSTEMS, AND METHODS, which claims the benefit of U.S. Provisional Application No. 62/729,297, filed Sep. 10, 2018, and entitled CATHETER STABILIZATION PLATFORM, SYSTEMS AND METHODS, which are incorporated herein in their entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. In some embodiments, an attachment for a catheter assembly may include a platform, which may include an upper surface and a bottom surface. In some embodiments, the bottom surface may be configured to contact skin of a patient. In some embodiments, at least a portion of the upper surface may be configured to support the catheter assembly. In some embodiments, the upper surface may support the catheter assembly at an angle with respect to skin of the patient that is approximately equal to an insertion angle of a catheter of the catheter assembly.

In some embodiments, the portion of the upper surface may be disposed at an angle with respect to the bottom surface of the platform or may be configured to be angled with respect to the skin of the patient. In some embodiments, the angle may be 30° or less than 30°. In some embodiments, the portion of the upper surface may include a groove, which may be configured to support a catheter adapter of the catheter assembly. In some embodiments, the portion of the upper surface may include at least one outer portion that is generally planar and configured to support a wing of the catheter assembly.

In some embodiments, the attachment may include snap feature coupled to the upper surface of the platform. In some embodiments, the snap feature may include an arm. In some embodiments, the arm may include a prong, which may extend inwardly from an inner surface of the arm. In some embodiments, the snap feature may include multiple arms. In some embodiments, the snap feature may include a first arm, a second arm, and a third arm. In some embodiments, the first arm and the second arm may be attached to the upper surface. In some embodiments, one or more of the first arm, the second arm, and the third arm may include the prong.

In some embodiments, the attachment may include a blunt cannula, which may extend distally from the snap feature. In some embodiments, the blunt cannula and the portion of the upper surface may provide a generally straight pathway for an instrument inserted distally through the attachment into the catheter assembly. In some embodiments, the instrument may include an additional catheter for fluid infusion or blood draw, a guidewire, a probe with a sensor, or a light tube for disinfection. In some embodiments, the blunt cannula may be disposed at a same angle or generally parallel to the portion of the upper surface. In some embodiments, the attachment may include an obturator, which may extend through the blunt cannula. In some embodiments, the obturator may include a sharp tip or a blunt tip, which may be configured to facilitate penetration of a septum of the catheter adapter by the blunt cannula.

In some embodiments, the attachment may include one or more push tabs, which may be coupled to the upper surface. In some embodiments, the attachment may include a bond pocket, which may be coupled to the snap feature. In some embodiments, the attachment may include an extension tube, which may include a proximal end and a distal end. In some embodiments, the distal end may be secured within the bond pocket. In some embodiments, the attachment may include a connector, which may be coupled to the proximal end of the extension tube.

In some embodiments, the bottom surface of the platform may include an arch, which may extend generally perpendicular to the blunt cannula. In some embodiments, the platform may include an aperture, which may be disposed beneath the blunt cannula. In some embodiments, the platform may be generally U-shaped and may not extend beneath the blunt cannula.

In some embodiments, the attachment may include a connector proximate the snap feature. In some embodiments, the connector may include one or more ribs. In some embodiments, the connector may include one or more wings. In some embodiments, the attachment may include an insert cap or a luer cap coupled to the connector.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
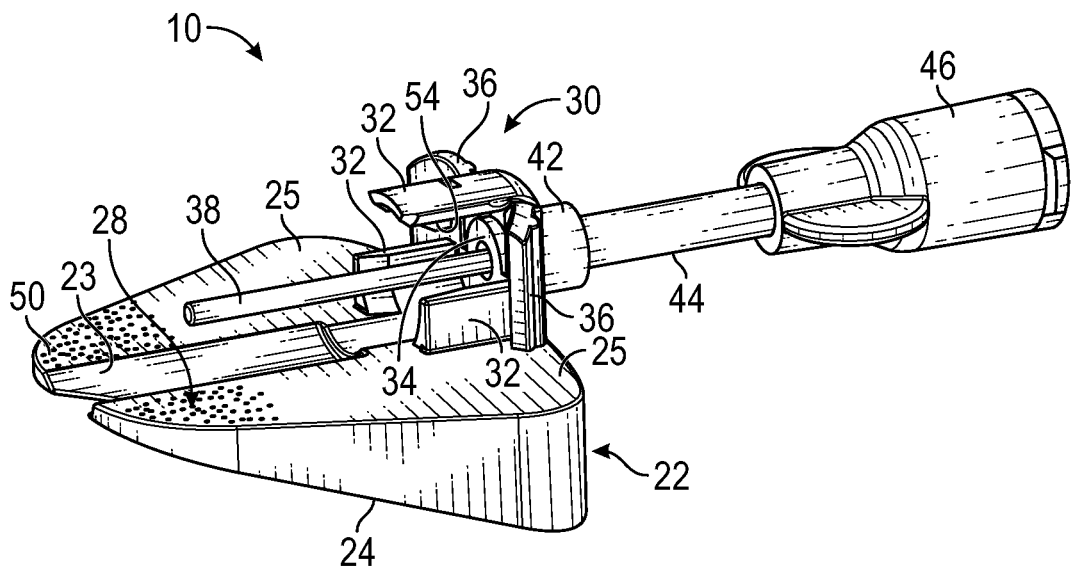
FIG. 1A is an upper perspective view of an example attachment, according to some embodiments.

Referring now to FIG. 1A-1D, an attachment 10 for a catheter assembly 12 is illustrated, according to some embodiments. In some embodiments, the attachment 10 may be coupled to a proximal end of the catheter assembly 12 and may support the catheter assembly 12 at an angle with respect to skin of a patient.

In some embodiments, the catheter assembly 12 may include a catheter adapter 16 and a catheter 18. In some embodiments, the catheter 18 may be secured within the catheter adapter 16 and may extend distally from a distal end 20 of the catheter adapter 16. In some embodiments, the catheter 18 may include a peripheral intravenous catheter ("PIVC"). In some embodiments, the catheter adapter 16 may include one or more wings 21. In some embodiments, the catheter assembly 12 may be integrated with an integrated extension tube or non-integrated without an extension tube.

In some embodiments, in order to place the catheter 18 within vasculature of the patient for fluid infusion and/or blood withdrawal, an introducer needle (not illustrated) and the catheter 18 may be inserted into the skin 19 of the patient at a shallow insertion angle with respect to the skin 19. In some embodiments, the insertion angle may be about 30° or less. In some embodiments, the introducer needle may be removed following confirmation that the catheter 18 is in the vasculature. In some embodiments, after the introducer needle is removed, the catheter assembly 12 may be coupled to the attachment 10.

In some embodiments, the attachment 10 may include a platform 22, which may be disposed between a portion of the catheter assembly 12 and the skin 19 to support the catheter assembly 12. In some embodiments, a bottom surface 24 of the platform 22 may be generally planar and may sit flat against the skin 19. In some embodiments, at least a portion of an upper surface 28 of the platform 22 may be angled with respect to the bottom surface 24 and/or the skin 19. In some embodiments, the portion of the upper surface 28 may be configured to support the catheter adapter 16 and/or one or more wings 21 of the catheter adapter 16 at an angle equal to or less than the insertion angle of the catheter 18.

In some embodiments, the portion of the upper surface 28 of the platform 22 may support the catheter assembly 12 in a position with the distal end 20 or nose of the catheter adapter 16 tilted downward toward the skin 19 of the patient and a proximal end 26 of the catheter adapter 16 tilted upward away from the skin 19 of the patient, which may facilitate insertion of an instrument through the attachment 10 and/or into the vasculature. In some embodiments, the instrument may include an additional catheter for fluid infusion or blood draw, a guidewire, a probe with a sensor, or a light tube for disinfection.

In some embodiments, the portion of the upper surface 28 may include a groove 23, in which the catheter adapter 16 may sit, and/or one or more outer portions 25. In some embodiments, each of the outer portions 25 may be generally planar and/or may support a particular wing 21.

Figure 1B:
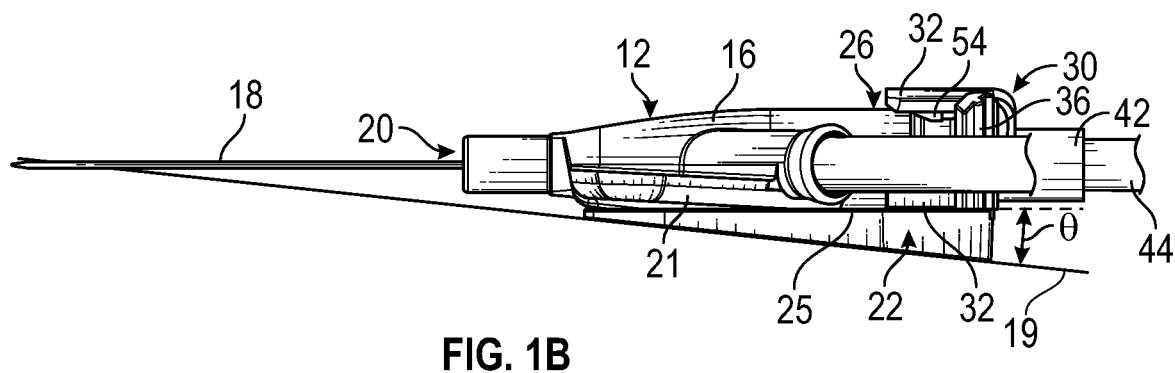
FIG. 1B is a side view of the attachment of FIG. 1A coupled with an example catheter assembly, illustrating an example catheter of the catheter assembly inserted into skin of a patient, according to some embodiments.
Figure 1C:
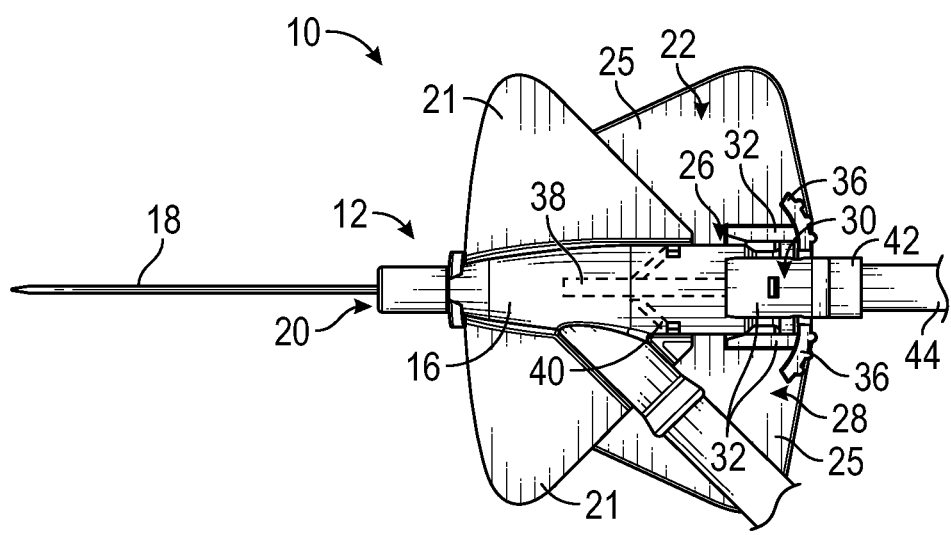
FIG. 1C is a top view of the attachment of FIG. 1A coupled with the catheter assembly, according to some embodiments.

In some embodiments, an angle θ of the portion of the upper surface 28 with respect to the bottom surface 24 and/or the skin 19 of the patient may be equal to or less than the insertion angle of the catheter 18. In some embodiments, the angle θ may be about 30°. In some embodiments, the angle θ may be 30° or less. FIG. 1B illustrates an example angle θ, according to some embodiments.

In some embodiments, the platform 22 may be constructed of a rigid material. In some embodiments, the platform 22 may be constructed of a soft, flexible material, which may conform to the skin 19 of the patient. In some embodiments, the platform 22 of the attachment 10 may be constructed in at least a two shot mold. In these embodiments, a first shot may form a snap feature 30 in a rigid or durable material, and a second shot may form the platform 22 in a soft, flexible material.

In some embodiments, the attachment 10 may include the snap feature 30 or another suitable coupling mechanism to couple the attachment 10 to the proximal end 26 of the catheter adapter 16. In some embodiments, the snap feature 30 may be disposed on the upper surface 28 of the platform 22. In some embodiments, the snap feature 30 may include one or more arms 32 configured to snap on to the catheter adapter 16. As illustrated in FIGS. 1A-1F, in some embodiments, the snap feature 30 may include three of the arms 32. In some embodiments, the snap feature 30 may include less than three of the arms 32 or more than three of the arms 32. In some embodiments, one or more of the arms 32 may extend distally from a base 34 of the snap feature 30. In some embodiments, one or more of the arms 32 may be attached to the upper surface 28 of the platform 22. In some embodiments, one or more of the arms 32 may extend from another portion of the attachment 10.

In some embodiments, the attachment 10 may include one or more push tabs 36, which may facilitate handling of the attachment 10 by the clinician and placement of the platform 22 underneath the catheter assembly 12 after the catheter 18 is positioned within the vasculature of the patient. In some embodiments, the push tabs 36 may include one or more grooves. In some embodiments, the push tabs 36 may extend outwardly from the snap feature 30 and/or may be attached to the upper surface 28. In some embodiments, the push tabs 36 may include pads.

In some embodiments, the attachment 10 may include a blunt cannula 38, which may be configured to extend through a proximal opening of the proximal end 26 of the catheter adapter 16 and penetrate a blood control septum 40 disposed within a lumen of the catheter adapter 16. In some embodiments, the blunt cannula 38 may extend distally from the base 34 of the snap feature 30. In some embodiments, the blunt cannula 38 may extend parallel to the portion of the upper surface 28 of the platform 22. In some embodiments, the blunt cannula 38 may be axially aligned with a central axis of the catheter assembly 12.

In some embodiments, the attachment 10 may include a bond pocket 42 or another suitable connector, which may extend proximally from the snap feature 30. In some embodiments, the bond pocket 42 may couple a distal end of an extension tube 44 to the snap feature 30. In some embodiments, the bond pocket 42 may extend outwardly from the base 34 of the snap feature 30.

In some embodiments, the attachment 10 may include a connector 46 disposed at a proximal end of the extension tube 44. In some embodiments, the connector 46 and the extension tube 44 may provide access to the catheter assembly 12 for fluid infusion and/or blood withdrawal at a location removed from an insertion site of the catheter 18, which may reduce a risk disturbing the catheter 18 in the insertion site. In some embodiments, the connector 46 may include a luer adapter or a non-luer adapter. In some embodiments, the connector 46 may include a needleless connector, which may be directly bonded to the proximal end of the extension tube 44. Alternatively, in some embodiments, a needleless connector may be coupled to the connector 46. In some embodiments, the extension tube 44 may be flexible, semi-flexible, or rigid.

In some embodiments, the extension tube 44 may be coupled to the attachment 10 and/or the connector 46 via various coupling mechanisms. In some embodiments, the extension tube 44 may be extruded. In some embodiments, the extension tube 44 may be adhered to the attachment 10 and/or the connector 46. In some embodiments, the extension tube 44 may be molded into the attachment 10 and/or the connector 46 and attachment using a multi-shot mold.

In some embodiments, a fluid pathway of the catheter assembly 12 may extend from a distal end of the catheter 18 through the proximal end 26 of the catheter adapter 16. In some embodiments, the fluid pathway of the catheter assembly 12 may include the central axis of the catheter assembly 12. In some embodiments, a fluid pathway of the attachment 10 may include one or more of the following: the blunt cannula 38, the base 34 of the snap feature 30, the bond pocket 42, the extension tube 44, and the connector 46. In some embodiments, a central axis of the fluid pathway of the catheter assembly 12 may be axially aligned with a central axis of the fluid pathway of the attachment 10, which may create a straight path through the catheter assembly 12 and the attachment 10. In some embodiments, the straight pathway may facilitate distal advancement of the instrument through the attachment 10 and the catheter assembly 12 and may reduce or eliminate bending of the instrument and/or catching of the instrument. In some embodiments, the instrument may be inserted into the attachment 10 through the connector 46 and/or advanced distally beyond the distal end of the catheter 18.

Figure 1D:
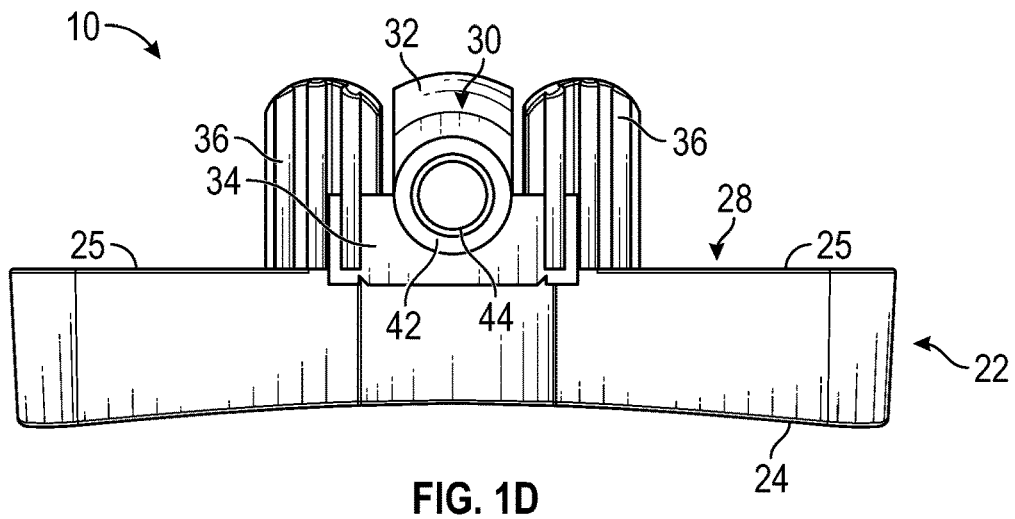
FIG. 1D is a proximal end view of the attachment of FIG. 1A, according to some embodiments.

As illustrated in FIG. 1D, in some embodiments, the bottom surface 24 may include an arch or curved surface, which may fit ergonomically against the skin 19 of the patient. In some embodiments, the arch may be oriented generally perpendicular to a proximal-distal direction and a longitudinal axis of the catheter assembly 12. In some embodiments, the arch may reduce pressure on the vasculature of the patient, which may reduce a likelihood of occlusion.

Figure 1E:
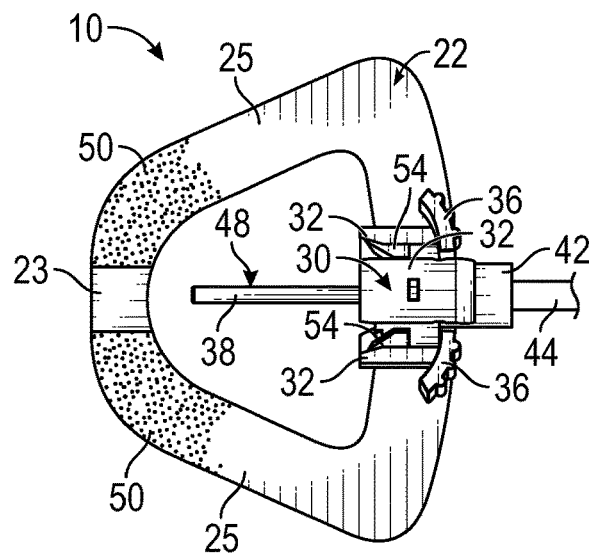
FIG. 1E is an upper perspective view of the attachment of FIG. 1A, illustrating an example aperture, according to some embodiments.

Referring now to FIG. 1E, in some embodiments, the platform 22 may include an aperture 48, which may decrease a surface area of the platform 22 in contact with the skin 19 of the patient and reduce a force of friction between the platform 22 and the wings 21 during coupling of the attachment 10 to the catheter assembly 12. In some embodiments, the aperture 48 may be enclosed. In some embodiments, the platform 22 having the aperture 48 may also reduce the force of friction between the platform 22 and the skin 19.

In some embodiments, a lubricant 50 may be added to at least a portion of the upper surface 28 of the platform 22 in order to reduce the force of friction between the platform 22 and the wings 21 and facilitate coupling of the attachment 10 to the catheter assembly 12. Additionally or alternatively, in some embodiments, the lubricant 50 may be added to an outer surface of all or a portion of the blunt cannula 38, which may reduce the force of friction between the blunt cannula 38 and the blood control septum 40.

Figure 1F:
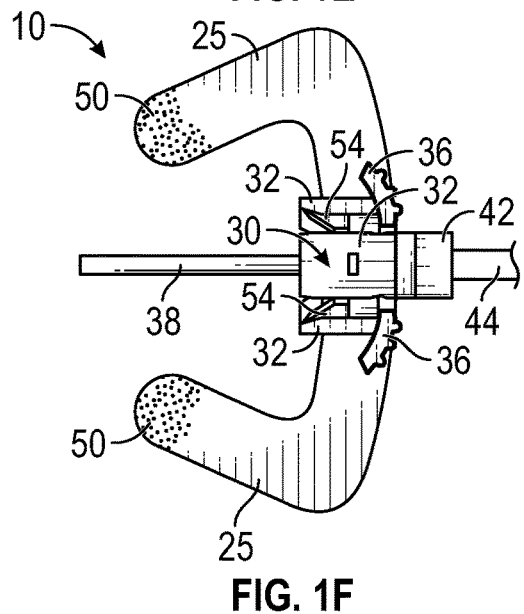
FIG. 1F is an upper perspective view of the attachment of FIG. 1A, illustrating an example U-shape, according to some embodiments.

Referring now to FIG. 1F, in some embodiments, the platform 22 may be generally U-shaped, which may decrease a surface area of the platform 22 in contact with the skin 19 of the patient and reduce the force of friction between the platform 22 and the wings 21 during coupling of the attachment 10 to the catheter assembly 12. In some embodiments, the platform 22 being generally U-shaped may also reduce the force of friction between the platform 22 and the skin 19.

Referring now to FIGS. 2A-2D, in some embodiments, the attachment 10 may not include the extension tube 44. In some embodiments, a connector 52 may be coupled to the snap feature 30, such as, for example, the base 34 of the snap feature 30. In some embodiments, the connector 52 may include a luer adapter or another suitable connector. In some embodiments, the connector 52 may be molded as part of the snap feature 30. In some embodiments, the connector 52 and the snap feature 30 may be monolithically formed as a single unit. In some embodiments, the connector 52 may be smooth and/or may include wings, as illustrated, for example, in FIG. 2A. In some embodiments, the connector 52 may include ribs, as illustrated, for example, in FIGS. 2B-2C.

Figure 2A:
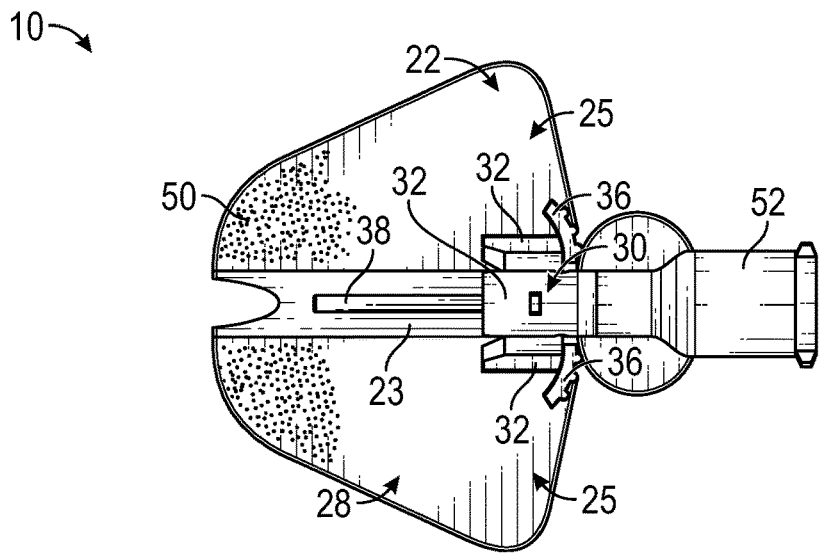
FIG. 2A is an upper perspective view of the attachment of FIG. 1A, illustrating an example connector proximate an example snap feature, according to some embodiments.
Figure 2B:
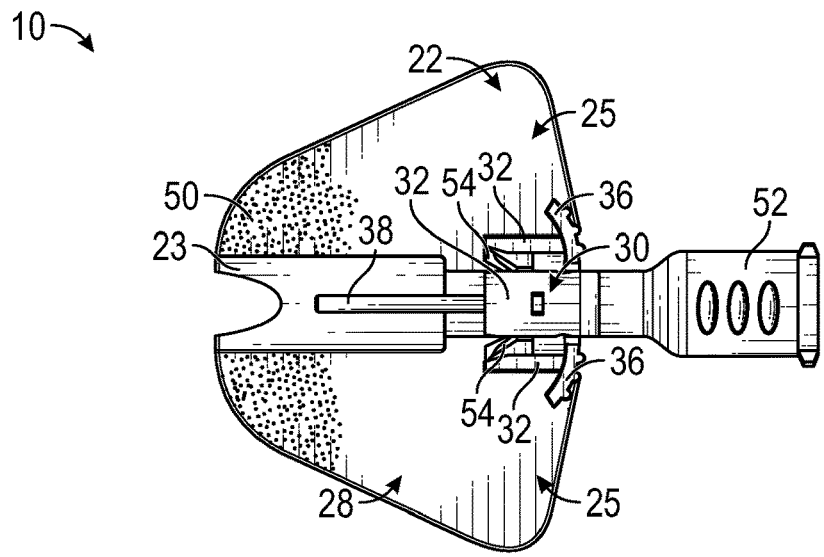
FIG. 2B is an upper perspective view of the attachment of FIG. 1A, illustrating the connector proximate the snap feature, according to some embodiments.
Figure 2C:
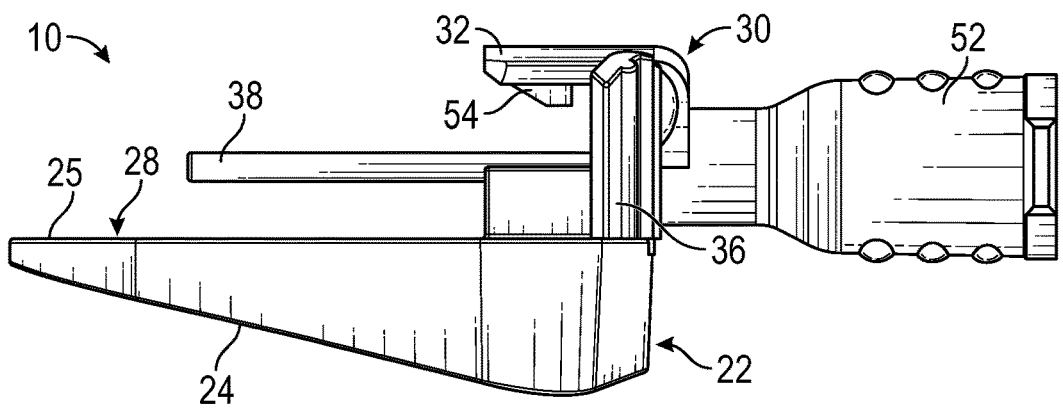
FIG. 2C is a side view of the attachment of FIG. 2B, according to some embodiments.
Figure 2D:
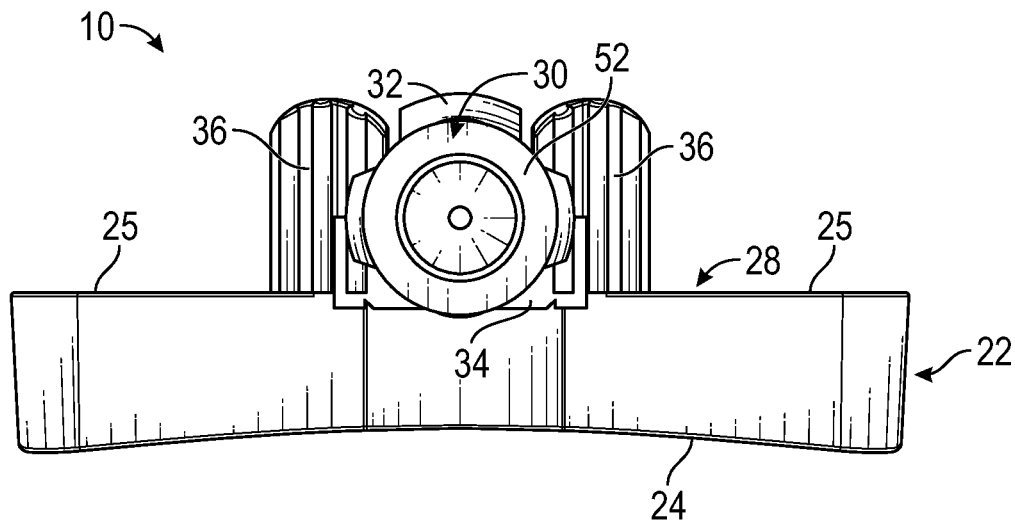
FIG. 2D is a proximal end view of the attachment of FIG. 2B, according to some embodiments.

In some embodiments, the snap feature 30 may include one or more prongs 54. In some embodiments, the prongs 54 may be positioned within one or more grooves of the catheter adapter 16 when the attachment 10 is coupled to the catheter assembly 12 in a snap fit. FIG. 2A illustrates the snap feature 30 having a single prong 54 disposed on a particular arm 32 of the snap feature 30, according to some embodiments. FIG. 2B illustrates the arms 32 each having a prong 54, which may improve a connection between the catheter adapter 16 and the attachment 10, according to some embodiments.

Figure 3A:
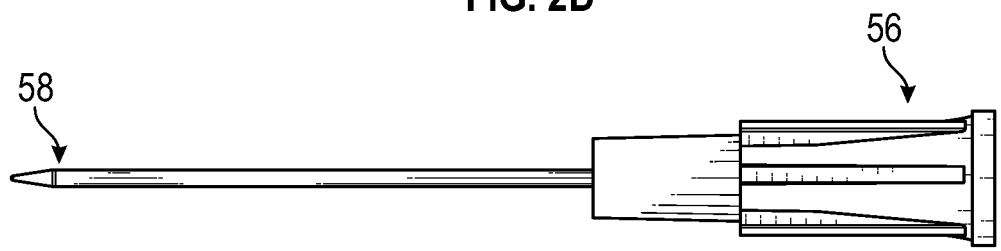
FIG. 3A is an upper perspective view of an example obturator, according to some embodiments.
Figure 3B:
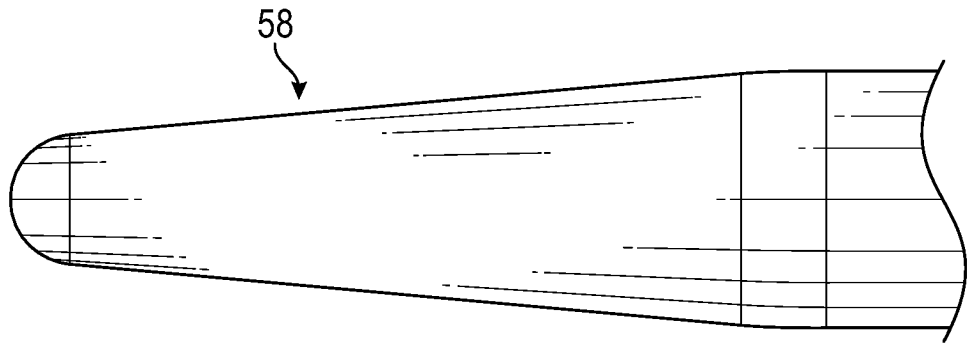
FIG. 3B is an upper perspective view of an example distal tip of the obturator of FIG. 3A, according to some embodiments.
Figure 3C:
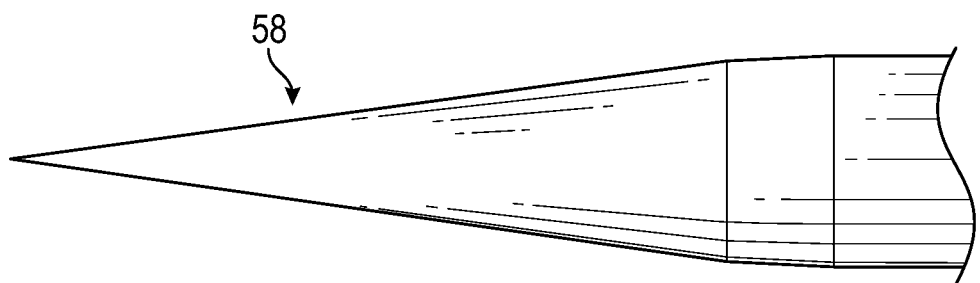
FIG. 3C is an upper perspective view of another example distal tip of the obturator of FIG. 3A, according to some embodiments.

Referring now to FIGS. 3A-3C, in some embodiments, the attachment 10 and the catheter assembly 12 may be configured to receive an obturator 56, which may facilitate insertion of the blunt cannula 38 through the blood control septum 40 of the catheter adapter 16. In some embodiments, the obturator 56 may include a round or bullet-shaped distal tip 58, as illustrated, for example, in FIG. 3B. In some embodiments, the obturator 56 may include a sharp or pointed distal tip 58, as illustrated, for example, in FIG. 3C. In some embodiments, the obturator 56 may be rigid or semi-rigid. In some embodiments, the obturator 56 may be constructed of metal or another suitable material.

In some embodiments, the blood control septum 40 may be pre-slit or may not be pre-slit. In some embodiments, the distal tip 58 may facilitate opening of the blood control septum 40. In some embodiments, the distal tip 58 may create a hole in the blood control septum 40, through which the blunt cannula 38 may extend. In some embodiments, in response to coupling of the attachment 10 to the catheter assembly 12, the obturator 56 may be proximally removed from the attachment 10. In some embodiments, in response to removal of the obturator 56 from the attachment 10, a needleless connector may be coupled to the connector 46 and/or the connector 52. In some embodiments, in response to removal of the obturator 56 from the attachment 10, the instrument may be threaded distally through the attachment 10 and/or the catheter assembly 12.

Figure 3D:
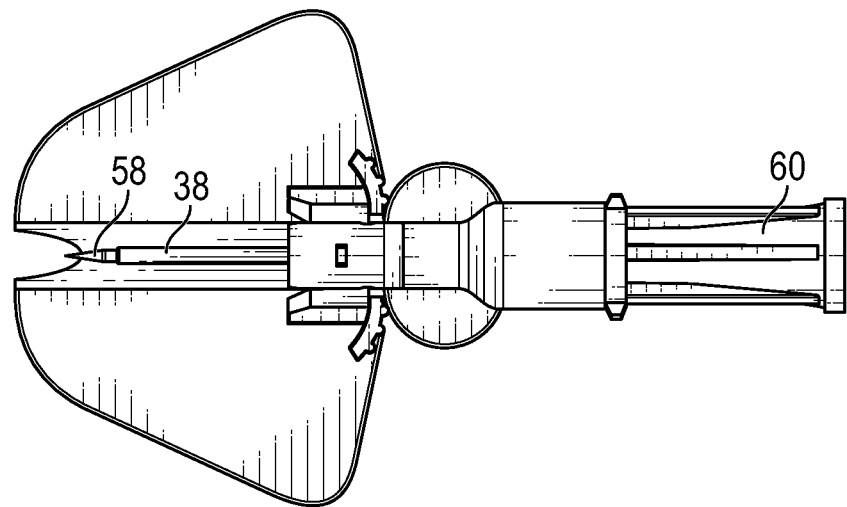
FIG. 3D is a top view of an example insert cap and the obturator of FIG. 3A threaded beyond a distal tip of an example blunt cannula, according to some embodiments.
Figure 3E:
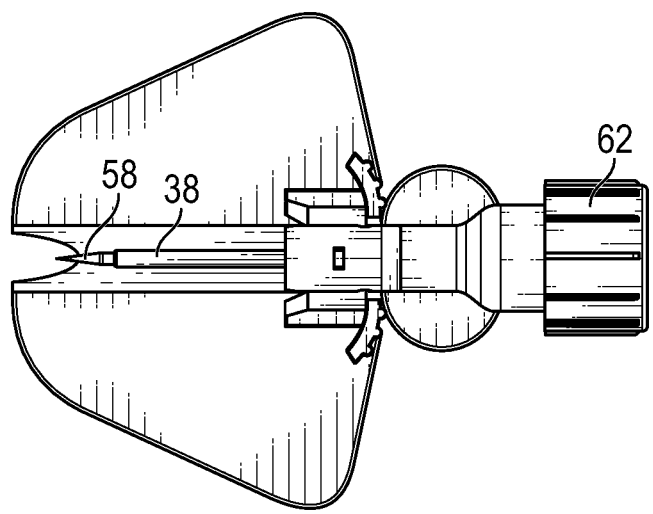
FIG. 3E is a top view of an example luer cap and the obturator of FIG. 3A threaded beyond the distal tip of the blunt cannula, according to some embodiments.

Referring now to FIG. 3D, in some embodiments, a proximal end of the obturator 56 may include an insert cap 60, which may be inserted snugly into the connector 52 and/or the connector 46 of FIGS. 1A-1F. Referring now to FIG. 3E, in some embodiments, a proximal end of the obturator 56 may include a luer cap 62, which may include a slip or thread male luer. Although FIGS. 3D-3E illustrate the obturator 56 being used without the extension tube 44, it is also contemplated that the obturator 56 may be used with and inserted through the extension tube 44 of FIGS. 1A-1F.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An attachment for a catheter assembly, the attachment comprising:
   a platform having a proximal end and opposing outer portions that extend distally from opposing sides of the proximal end to thereby form a U shape, each outer portion having an upper surface for supporting a wing of a catheter adapter of the catheter assembly and a bottom surface configured to contact skin of a patient;
   a snap feature comprising a base that extends upwardly from the proximal end of the platform and arms that extend distally from the base, the arms being configured to extend around a proximal end of the catheter adapter to couple the catheter assembly to the attachment while the wings of the catheter adapter are supported by the upper surface of each outer portion; and
   a blunt cannula extending distally from the base of the snap feature and between the arms, the blunt cannula being configured to be inserted into the proximal end of the catheter adapter of the catheter assembly when the catheter assembly is coupled to the attachment via the arms of the snap feature.

2. The attachment of claim 1, wherein the upper surface of each outer portion slopes downwardly towards a distal end of each outer portion to thereby cause the catheter adapter to be angled distally downward when the wings of the catheter adapter are supported by the upper surface of each outer portion.

3. The attachment of claim 2, wherein the upper surface of each outer portion slopes downwardly towards the distal end of each outer portion at an angle between 20° and 30° relative to the bottom surface of each outer portion.

4. The attachment of claim 1, wherein the arms comprise a first arm and a second arm positioned on opposing sides of the base and a third arm positioned at a top of the base.

5. The attachment of claim 1, further comprising:
   push tabs that extend upwardly from the proximal end of the platform and are positioned on opposing sides of the base of the snap feature.

6. The attachment of claim 1, wherein at least one of the arms comprises a prong.

7. The attachment of claim 1, wherein a distal end of the blunt cannula extends distally beyond a distal end of each outer portion.

8. The attachment of claim 1, further comprising:
   a bond pocket coupled to the snap feature;
   an extension tube having a proximal end and a distal end, wherein the distal end is secured within the bond pocket; and
   a connector coupled to the proximal end of the extension tube.

9. The attachment of claim 1, further comprising a connector proximate the snap feature.

10. The attachment of claim 9, wherein the connector comprises a plurality of ribs.

11. The attachment of claim 9, wherein the connector comprises wings.

12. The attachment of claim 9, further comprising an insert cap or a luer cap coupled to the connector.

13. The attachment of claim 1, further comprising an obturator extending through the blunt cannula.

14. The attachment of claim 13, wherein the obturator has a sharp tip.

15. The attachment of claim 13, wherein the obturator has a blunt tip.

16. A catheter system comprising:
   a catheter assembly comprising a catheter adapter having wings on opposing sides of the catheter adapter; and
   an attachment for the catheter assembly, the attachment comprising:
     a platform having a proximal end and opposing outer portions that extend distally from opposing sides of the proximal end to thereby form a U shape, each outer portion having an upper surface for supporting one of the wings of the catheter adapter and a bottom surface configured to contact skin of a patient;

a snap feature comprising a base that extends upwardly from the proximal end of the platform and arms that extend distally from the base, the arms being configured to extend around a proximal end of the catheter adapter to couple the catheter assembly to the attachment while the wings of the catheter adapter are supported by the upper surface of each outer portion; and a blunt cannula extending distally from the base of the snap feature and between the arms, the blunt cannula being configured to be inserted into the proximal end of the catheter adapter when the catheter assembly is coupled to the attachment via the arms of the snap feature.

17. The catheter system of claim 16, wherein the upper surface of each outer portion slopes downwardly towards a distal end of each outer portion to thereby cause the catheter adapter to be angled distally downward when the wings of the catheter adapter are supported by the upper surface of each outer portion.

18. The catheter system of claim 17, wherein the upper surface of each outer portion slopes downwardly towards the distal end of each outer portion at an angle between 20° and 30° relative to the bottom surface of each outer portion.

19. The catheter system of claim 16, wherein the arms comprise a first arm and a second arm positioned on opposing sides of the base and a third arm positioned at a top of the base.

20. The catheter system of claim 16, further comprising:

push tabs that extend upwardly from the proximal end of the platform and are positioned on opposing sides of the base of the snap feature.

* * * * *